United States Patent [19] [11] 4,078,012
Blewett et al. [45] Mar. 7, 1978

[54] OLEFIN METATHESIS CATALYSTS AND PROCESS UTILIZING SAME

[75] Inventors: Charles W. Blewett, Ft. Mitchell, Ky.; William R. Garrett, Jr., Cincinnati, Ohio

[73] Assignee: Emery Industries, Inc., Cincinnati, Ohio

[21] Appl. No.: 743,935

[22] Filed: Nov. 22, 1976

[51] Int. Cl.² .................................................. C07C 3/62
[52] U.S. Cl. ............................ 260/683 D; 252/429 B; 260/666 A; 260/668 R; 260/669 R
[58] Field of Search .......... 260/683 D, 666 A, 668 R, 260/669 R; 252/429 B

[56] References Cited

U.S. PATENT DOCUMENTS 3,778,385 12/1973 Zuech ............................. 252/429 B
3,790,543 2/1974 Lehnert et al. .................. 252/429 B

OTHER PUBLICATIONS

Ichikawa et al, Journal of Organic Chemistry, vol. 41, No. 15, pp. 2633–2635, 7-23-76.

*Primary Examiner*—Delbert E. Gantz
*Assistant Examiner*—C. E. Spresser
*Attorney, Agent, or Firm*—Gerald A. Baracka; John D. Rice

[57] ABSTRACT

Improved homogeneous metathesis catalysts are obtained by the use of a trivalent phosphorus modifying agent with a cocatalyst comprised of tungsten hexachloride and an organotin compound. These modified catalyst systems give significantly increased conversions and excellent product selectivity when used for olefin metathesis.

8 Claims, No Drawings

OLEFIN METATHESIS CATALYSTS AND PROCESS UTILIZING SAME

BACKGROUND OF THE INVENTION

Olefin metathesis reactions (also referred to as dismutation or disproportionation reactions) wherein an olefin is converted to a product having a higher or lower carbon number than the starting material are known. These reactions are of considerable interest because of the versatility of the reaction and the numerous olefinic hydrocarbons available from petrochemical sources which are suitable for use in the reaction to yield useful products. While both heterogeneous and homogeneous catalysts can be used for these reactions the heterogeneous catalysts generally require higher reaction temperatures and pressures and give lower selectivity, particularly when using higher olefins. For these reasons recent emphasis has been to the development of new and improved homogeneous catalyst systems.

Homogeneous catalysts presently known and available are largely based on tungsten and molybdenum compounds, such as tungsten hexachloride, molybdenum pentachloride or tungsten oxytetrachloride, in combination with an organometallic compound or Group 1a, 3a or 4a of the Periodic Table (Handbook of Chemistry and Physics, 56th Edition, 1975-76) most notably lithium, aluminum, germanium or tin. For example, British patent specification No. 1208068 discloses a homogeneous disproportionation catalyst system of molybdenum pentachloride or tungsten hexachloride and an organometallic compound of germanium or tin. The preferred catalyst for the process is derived from tungsten hexachloride and tetra-n-butyl tin. A binary catalyst system of tungsten hexachloride and n-butyllithium is also described by J. Wang et al. in the Journal of Organic Chemistry, Vol. 33, No. 10 (1968) at pages 3794-6. A tertiary catalyst system consisting of a tungsten or molybdenum salt, an organotin compound and a boron halide or its etherate is also disclosed in U.S. Pat. No. 3,901,866. The catalysts are employed to polymerize cyclopentene to obtain cis- and trans-polypentenamers. The disproportionation of olefins in the homogeneous phase employing a catalyst consisting of an alcoholate of molybdenum or tungsten and an organometallic reducing agent is described in U.S. Pat. No. 3,855,340.

V. M. Kothari et al. in the Journal of Organic Chemistry, Vol. 35, No. 20 (1971) at pages 2951-53 report that triphenylphosphine hinders the metathesis of 2-pentene using a tungsten hexachloride/ethylaluminum dichloride cocatalyst system. It has also been reported by K. Ichikawa et al. in the Journal of Organic Chemistry, Vol. 41, No. 15 (1976) at pages 2633-35, that tri-n-butylphosphine is not an effective additive for the tungsten hexachloride/tetrabutyl tin catalyzed metathesis of 1-octene. Whereas esters, acetronitrile, phenylacetylene, dicyclopentadiene and ethers were observed to increase the selectivity of the metathesis by depressing side reactions, no such improvement was obtained when tri-n-butylphosphine was employed as the additive.

It is possible with the known homogeneous catalyst systems to obtain high product selectivity, however, this is typically accompanied by low conversion of the olefin. When measures are taken to increase conversion there is typically a corresponding decrease in the product selectivity. Also, with the previously reported tungsten/organotin cocatalysts there is considerable inconsistency in the results obtained so that even when optimum molar ratios and reaction conditions are employed drastically different conversion and product selectivity can be obtained from run to run. These variations have generally been attributed to indefinable variations in the tungsten compound. For example, tungsten compounds obtained from different suppliers and manufactured to the same product specifications can give markedly different results. Also, variations are often noted with tungsten reagents which have been stored even for a short period of time following all of the recommended storage procedures. Especially in the case of tungsten hexachloride, widely divergent results are obtained with reagents obtained from different suppliers even though the products are, by all measurable standards, identical or when the reagent has been stored for a period of time even though all the prescribed storage precautions have been strictly adhered to. In practice it has not been possible to obtain consistently high conversion of $\alpha$-olefins with high selectivity to the desired product using heretofore known tungsten/organotin homogeneous catalyst systems.

It would be extremely advantageous therefore if it were possible to consistently obtain increased conversions with high product selectivity in $\alpha$-olefin metathesis reactions employing a homogeneous catalyst system. It would be even more desirable if such metathesis reactions consistently gave high conversions with greater than 95% selectivity and if the catalysts could be obtained by simple modification of a tungsten/organotin cocatalyst with readily available and economical modifying agents. It would be even more advantageous if the improved catalysts and results were obtained without regard to the source and storage history of the tungsten compound. These and other desirable features are now fully realized with the modified homogeneous olefin metathesis catalysts which will be described more fully below.

SUMMARY OF THE INVENTION

We have now quite unexpectedly discovered improved homogeneous catalysts obtained by the addition of a trivalent phosphorus compound to a tungsten hexachloride/organotin cocatalyst. Useful trivalent phosphorus compounds include phosphines and phosphites.

In addition to significantly improving the conversion and product selectivity the modified catalysts of this invention also, quite unexpectedly, make it possible to obtain consistent results without regard to the source or storage history of the tungsten hexachloride. This latter feature is particularly advantageous since it eliminates variations which have heretofore been observed using tungsten hexachloride from different suppliers or when it was necessary to store the tungsten reagent after the original container had been opened. It is totally unexpected and surprising that much improved and highly effective homogeneous catalyst systems are obtained by modification with trivalent phosphorus compounds in view of the results obtained by V. M. Kothari et al. and K. Ichikawa et al. and reported in the articles cited above.

The improved catalysts of this invention consist of tungsten hexachloride and an organotin compound which is preferably a tetraalkyl tin compound wherein the alkyl groups contain from 1 to 8 carbon atoms. The molar ratio of organotin compound to tungsten hexachloride will range from about 0.4:1 to 1.5:1. Especially useful modified catalysts are obtained using tungsten hexachloride at a molar ratio (tin compound:tungsten hexachloride) of 0.9:1 to 1.1:1. The trivalent phosphorus modifier corresponds to the structural formula

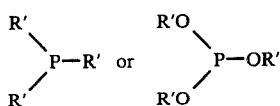

where R' is an alkyl, cycloalkyl, phenyl, alkyl-substituted phenyl, benzyl or other aralkyl radical. The molar ratio of the phosphorus modifying agent to tungsten hexachloride will range from 0.25:1 to 0.75:1. Trialkylphosphines and triphenylphosphine are especially useful modifying agents for this invention. The homogeneous catalysts of this invention find general application for all olefin metathesis reactions. They can be used to metathesize both internal and terminal olefinic materials containing up to about 50 carbon atoms. The catalysts are especially useful for the metathesis of $\alpha$-olefins or mixtures of $\alpha$-olefins containing 1 to 30 carbon atoms and, more preferably, 4 to 16 carbon atoms. The catalyst is employed in an amount such that from about 0.0003 mole to about 0.1 mole tungsten hexachloride is present per mole of the olefin.

DETAILED DESCRIPTION

The present invention relates to improved olefin metathesis catalysts and to processes utilizing these catalysts. In general, the modified catalysts of this invention are useful in a wide variety of metathesis reactions but they are most useful in reactions employing olefinic hydrocarbons of the general formula

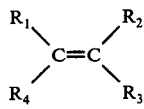

where $R_1$ is an alkyl group containing from 1 to 40 carbon atoms, a cycloalkyl or alkyl-substituted cycloalkyl group containing 3 to 20 carbon atoms, phenyl, a $C_{1-20}$ alkyl-substituted phenyl radical or radical of the formula

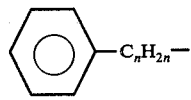

where $n$ is an integer from 1 to 20 and $R_2$, $R_3$ and $R_4$ are, independently, hydrogen or a radical as defined for $R_1$ such that the total number of carbon atoms does not exceed about 50. A pure olefin may be employed or a mixture of the same or different types of olefins can be used with the catalysts of this invention.

The modified homogeneous catalysts find particular applicability in processes where an $\alpha$-olefin or mixture of $\alpha$-olefins are metathesized. These $\alpha$-olefins are readily available from petrochemical sources and have the general formula

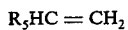

$$R_5HC=CH_2$$

where $R_5$ is an alkyl group having from 1 to 30 carbon atoms and, more preferably, 4 to 16 carbon atoms. Suitable $\alpha$-olefins of the above type include but are not limited to propylene, 1-butene, 1-pentene, 1-hexene, 1-octene, 1-nonene, 1-decene, 1-dodecene, 1-tetradecene and the like. The metathesis of 1-decene, for example, would yield 9-octadecene and can be depicted as follows:

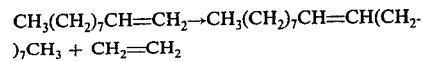

$$2\ CH_3(CH_2)_7CH=CH_2 \rightarrow CH_3(CH_2)_7CH=CH(CH_2)_7CH_3 + CH_2=CH_2$$

Where a mixture of $\alpha$-olefins is employed, such as with a 50/50 mixture of 1-octene and 1-decene, cross metathesis would occur in accordance with the equation:

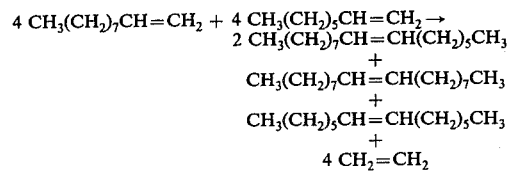

$$4\ CH_3(CH_2)_7CH=CH_2 + 4\ CH_3(CH_2)_5CH=CH_2 \rightarrow$$
$$2\ CH_3(CH_2)_7CH=CH(CH_2)_5CH_3$$
$$+$$
$$CH_3(CH_2)_7CH=CH(CH_2)_7CH_3$$
$$+$$
$$CH_3(CH_2)_5CH=CH(CH_2)_5CH_3$$
$$+$$
$$4\ CH_2=CH_2$$

The present improved catalysts consist of tungsten hexachloride and an organotin compound modified with trivalent phosphorus compound. While tungsten hexachloride is preferred because of its commercial availability and the efficiency of catalysts obtained therewith other tungsten compounds, particularly tungsten halides, can be used. For example, tungsten hexabromide, tungsten hexaiodide or tungsten hexafluoride can be advantageously employed as can the penta- or tetrahalides of tungsten wherein the halogen is preferably chlorine but can also be iodine, fluorine or bromine.

The organotin compound will correspond to the general formula

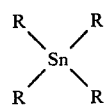

where R is an alkyl group containing from 1 to 16 carbon atoms, a cycloalkyl group containing from 3 to 8 carbon atoms, benzyl, phenyl or an alkyl-substituted phenyl group containing from 7 to 12 carbon atoms. Suitable organotin compounds of the above type include tetramethyl tin, dimethyldiethyl tin, tetraethyl tin, diethyldibutyl tin, tetrabutyl tin, tetraoctyl tin, tetranonyl tin, tetracyclohexyl tin, tetrabenzyl tin, tetraphenyl tin and the like. Especially useful organotin compounds for the preparation of the modified catalyst systems of this invention are tetraalkyl tin compounds wherein the alkyl group contains from 1 to 8 carbon atoms. In terms of the above formula R would be a $C_{1-8}$ alkyl group. The molar ratio of the organotin compound to the tungsten compound can range from about 0.4:1 to 1.5:1, however, it is preferred that 0.8 to 1.2 moles organotin compound per mole tungsten compound be used. Especially useful homogeneous catalyst systems of this invention which give markedly superior results are obtained using a tetra($C_{1-8}$ alkyl) tin compound with tungsten hexachloride at a mole ratio (tin component:tungsten component) of 0.9:1 to 1.1:1.

A trivalent phosphorus compound is employed as the modifying agent with the tungsten hexachloride and organotin compound to obtain the improved homogeneous metathesis catalysts. The trivalent phosphorus compounds correspond to the structural formula

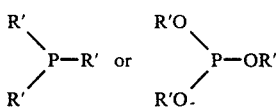

wherein R' is an alkyl radical, branched or straight-chain, containing from 1 to 16 carbon atoms, a cycloalkyl radical containing from 3 to 8 carbon atoms, phenyl or an alkyl-substituted phenyl radical wherein the alkyl substituent(s) contain(s) from 1 to 8 carbon atoms and benzyl or other aralkyl radical having from 8 to 20 carbon atoms. It is not necessary that all of the R' radicals be the same. Illustrative of the phosphines and phosphites which can be used for this invention are the following: trimethylphosphine, triethylphosphine, triisopropylphosphine, tri-n-propylphosphine, tri-n-butylphosphine, trihexylphosphine, trioctylphosphine, tri-2-ethylhexylphosphine, tridecylphosphine, tridodecylphosphine, triphenylphosphine, tricyclohexylphosphine, tribenzylphosphine, trimethylphosphite, triethylphosphite, triisopropylphosphite, tri-n-propylphosphite, tri-n-butylphosphite, trihexylphosphite, trioctylphosphite, tri-2-ethylhexylphosphite, tridecylphosphite, tridodecylphosphite, triphenylphosphite, tribenzylphosphite, tricyclohexylphosphite and the like. Triphenylphosphine and trialkylphosphines wherein the alkyl group contains from 2 to 6 carbon atoms are especially useful for this invention.

The molar ratio of the phosphine or phosphite modifier to the tungsten component will range from about 0.1:1 to 0.95:1, however, it is especially useful if about 0.25 to 0.75 moles of the phosphorus compound is used per mole tungsten hexachloride. Especially effective homogeneous catalysts are obtained with triphenylphosphine or a tri-($C_{2-6}$ alkyl) phosphine with tungsten hexachloride and a tetra-($C_{1-8}$ alkyl) tin compound. These catalysts are particularly useful for the metathesis of α-olefins and consistently give high conversions with 95+% selectivity.

To conduct metathesis reactions employing the modified and improved catalysts of this invention a wide variety of reaction conditions can be employed. In general, the reaction conditions are the same as those described in the prior art and reference may be had thereto for more details. Operating temperatures can vary over a wide range from about 50° C to about 220° C, however, the reaction is most generally conducted at a temperature of about 90° to 180° C. The reaction can be conducted in the presence or absence of an inert hydrocarbon diluent such as benzene, toluene, xylene or the like. Paraffinic and cycloparaffinic hydrocarbons such as cyclohexane, methylcyclohexane, pentane, hexane, isooctane and the like can also be used for this purpose. While it may sometimes be advantageous to use diluents with high melting olefins or olefin mixtures, diluents are not necessary. The metathesis reaction can be conducted over a wide range of operating pressures varying from subatmospheric to superatmospheric. The pressure will generally be governed by the particular olefin or olefin mixture used and other operating conditions. While operating pressures can range up to about five atmospheres or higher, whenever possible the reaction is conducted at atmospheric pressure or as close thereto as feasible, especially when metathesizing α-olefins, since this facilitates removal of ethylene which drives the reaction. The reaction is generally conducted under an inert atmosphere of nitrogen, argon or helium and precautions are taken to exclude moisture from the system. Using these reaction conditions it is possible to consistently obtain high conversions and 95+% selectivity and to minimize, and in some cases completely eliminate, variations due to the origin of the tungsten hexachloride.

The modified catalysts of this invention are extremely effective when employed in metathesis reactions even at very low levels. High conversions of α-olefins and high product selectivity are obtained when there is present an amount as low as 0.0003 mole tungsten component per mole of the olefin to be metathesized. While there is theoretically no upper limit to the amount of catalyst which can be used, there is generally no advantage in using amounts much greater than about 0.1 mole tungsten component per mole olefin. Most generally the tungsten component will range from about 0.0006 to about 0.05 mole per mole of the olefin, particularly when metathesizing α-olefins.

In a typical batch laboratory preparation the desired amount of the tungsten compound is combined with the olefin to be metathesized in an inert atmosphere followed by the addition of the modifying agent. The organotin compound is then charged and the reactor and its contents heated to the desired temperature and pressurized, if desired. Samples are periodically removed from the reaction mixture and analyzed to follow the reaction.

Numerous modifications of this procedure are, however, possible. For example, the metathesis reaction can be conducted as a continuous or semi-continuous operation. Also, it is possible to add the catalyst components to the system as a solution in a suitable solvent. This procedure is particularly advantageous in continuous and semi-continuous operations since it facilitates handling and metering the various catalyst components into the system. It is also possible to combine two or more of the catalyst components prior to introduction into the reaction mixture even though maximum catalyst efficiency appears to be obtained when the components are admixed in the above-described step-wise manner. Still other modifications will be obvious to those skilled in the art and are within the scope of the present invention as will be evident from the following examples.

EXAMPLE I

Tungsten hexachloride 2.2 millimoles was weighed into a glass reactor under a nitrogen atmosphere and 3.5 moles 1-decene then added. The solution was stirred under nitrogen for about 15 minutes and 0.5 millimole tri-n-butylphosphine added followed by stirring for about 5 minutes and the addition of 2.2 millimoles tetrabutyl tin. The reaction mixture was then heated to 90° C while maintaining the nitrogen atmosphere. After 30 minutes a sample was removed from the reactor and chromatographic analysis indicated 65% conversion of the 1-decene with 97% selectivity to the desired 9-octadecene. By continuing the reaction at 90° C for an additional 2 hours the conversion was increased to 73% without any appreciable decrease in the percent selectivity.

EXAMPLE II

In a manner similar to that described in Example I 1-decene was metathesized to produce 9-octadecene. For this reaction, 3.5 moles 1-decene was combined with 2.2 millimoles tungsten hexachloride followed by the addition of 0.5 millimole triphenylphosphine and 2.2 millimoles tetrabutyl tin. The temperature of reaction was 90° C. Conversion of 1-decene and selectivity to the 9-octadecene was followed by chromatographic analysis of samples taken at 30, 60 and 90 minute intervals with the following results:

| Reaction Time: | % Conversion | % Selectivity |
|---|---|---|
| 30 minutes | 77 | 97 |
| 60 minutes | 83 | 97 |
| 90 minutes | 84 | 96 |

EXAMPLE III

Example I was repeated except that the tri-n-butylphosphine was increased to 1.1 millimoles. For this run the reaction temperature was maintained at 110° C for one hour after which time 75% conversion of the 1-decene was obtained with 99% selectivity to the desired 9-octadecene. When the temperature was increased to 175° C and the reaction continued for two additional hours, the olefin conversion was increased while maintaining 99% selectivity.

EXAMPLE IV

To demonstrate the effect of varying the amount of the modifier the following experiments were conducted in accordance with the procedure of Example I except that the modifying agent was triphenylphosphine and the olefin was 1-octene (freshly distilled). The molar ratio of the tetrabutyl tin to tungsten hexachloride was 1:1 for all of these runs, however, the ratio of the phosphine to tungsten hexachloride ranged from 0.25:1 up to 0.75:1. The metatheses were conducted at 110°–120° C and the following results obtained:

| Molar ratio (phosphine:$WCl_6$) | Reaction Time (Minutes) | Conversion (%) | Selectivity (%) |
|---|---|---|---|
| 0.125:1 | 300 | 40 | 96.2 |
| 0.5:1 | 90 | 54 | 99+ |
|  | 240 | 78 | 98.7 |
| 0.75:1 | 145 | 39 | 99 |

By increasing the temperature of these reactions it was possible to increase the olefin conversion without appreciably decreasing the selectivity. For example, in the run using the catalyst having a molar ratio of phosphine to $WCl_6$ of 0.5:1, when the temperature was increased to 140° C and the reaction continued to 300 minutes (total time) the conversion was increased to 84% with 98.8% selectivity.

EXAMPLE V

7-Tetradecene and 9-octadecene were cross-metathesized employing a homogeneous modified catalyst. For the reaction, 1 mole 7-tetradecene and 1 mole 9-octadecene were combined in the reactor with 13 millimoles tungsten hexachloride. Triphenylphosphine (6.5 millimoles) was then charged to the reactor followed by the addition of 13 millimoles tetrabutyl tin. The reaction was conducted at 115° C and after 330 minutes reaction, near equilibrium conversion of the olefins was obtained with high selectivity to the equilibrium mixture of 1-part 7-tetradecene, 1 part 9-octadecene and 2 parts 7-hexadecene. When the experiment was repeated in an identical manner but using an unmodified catalyst (13 millimoles tungsten hexachloride with 13 millimoles tetrabutyl tin) conversion of the olefins was significantly greater than the theoretical equilibrium conversion due to the lower selectivity of the reaction to the desired cross-metathesized products.

EXAMPLE VI

Following the procedure of Example I 1-decene (3.5 moles) was metathesized. The catalyst consisted of 2.2 millimoles tungsten hexachloride, 0.5 millimole triphenylphosphite and 2.2 millimoles tetrabutyl tin. After 2 hours reaction at 90° C the conversion was 60% with 98% selectivity.

EXAMPLE VII

To demonstrate the superior results obtained with the modified catalysts of this invention the following experiment using an unmodified tetrabutyl tin/$WCl_6$ catalyst was conducted. For this reaction the 1-decene (3.5 moles) was combined with 2.2 millimoles freshly opened reagent grade tungsten hexachloride and 2.2 millimoles tetrabutyl tin and the reaction mixture heated to 90° C. The conversion and selectivity were determined after 30, 90 and 150 minutes and the following results were obtained:

| Reaction Time: | % Conversion | % Selectivity |
|---|---|---|
| 30 minutes | 18 | 99 |
| 90 minutes | 21 | 99 |
| 150 minutes | 21 | 99 |

While increased conversion of the olefin can be obtained by raising the reaction temperature there is a corresponding significant decrease in the selectivity of the reaction. For example, at 125° C and 150° C, the conversions were increased to about 50% and 80% but the selectivities were only 52% and 38% respectively. It is evident by a comparison of the above data with the results of the preceeding Examples that under the same conditions much improved conversion of α-olefins can be obtained using the modified catalysts of this invention without adversely affecting the product selectivity.

We claim:

1. A process for metathesizing olefins which comprises contacting an olefin of the general formula

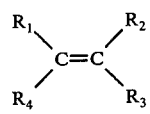

where $R_1$ is an alkyl group containing from 1 to 40 carbon atoms, a cycloalkyl or alkyl-substituted cycloalkyl group containing 3 to 30 carbon atoms, phenyl, a $C_{1-20}$ alkyl-substituted phenyl radical or racidal of the formula

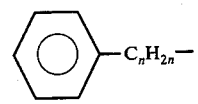

where $n$ is an integer from 1 to 20 and $R_2$, $R_3$ and $R_4$ are, independently, hydrogen or a radical as defined for $R_1$ such that the total number of carbon atoms in the olefin does not exceed about 50, with a homogeneous catalyst at a temperature from about 50° C to about 220° C under substantially anhydrous conditions, said homogeneous catalyst consisting essentially of:

a. tungsten hexachloride;

b. an organotin compound of the formula

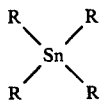

where R is an alkyl group containing from 1 to 6 carbon atoms, a cycloalkyl group containing from 3 to 8 carbon atoms, benzyl, phenyl or an alkyl-substituted phenyl group having from 7 to 12 carbon atoms; and c. a trivalent phosphorus compound, the molar ratio of (b) to (a) ranging from 0.4:1 to 1.5:1 and the molar ratio of (c) to (a) ranging from 0.1:1 to 0.95:1; said catalyst employed in an amount so that from about 0.0003 to about 0.1 mole tungsten hexachloride is present per mole of the olefin.

2. The process of claim 1 conducted at a temperature in the range 90° C to 180° C and wherein the olefin is an α-olefin or mixture of α-olefins and from about 0.0006 mole to about 0.05 mole tungsten hexachloride is present per mole α-olefin.

3. The process of claim 1 wherein (b) is a tetraalkyl tin compound wherein the alkyl groups containing from 1 to 8 carbon atoms, (c) is a compound corresponding to the formula

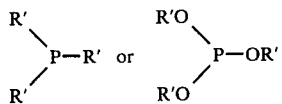

where R' is an alkyl radical having from 1 to 16 carbon atoms, a cycloalkyl group having from 3 to 8 carbon atoms, phenyl, a $C_{1-8}$ alkyl-substituted phenyl radical, benzyl or an aralkyl radical containing 8 to 20 carbon atoms, the molar ratio of (b) to (a) ranges from about 0.8:1 to 1.2:1 and the molar ratio of (c) to (a) is between 0.25:1 and 0.75:1.

4. The process of claim 3 wherein the olefin is an α-olefin or mixture of α-olefins of the general formula

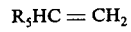

where $R_5$ is an alkyl group having from 1 to 30 carbon atoms and the active catalyst specie is formed in situ by first combining the olefin with the tungsten hexachloride and then adding the trivalent phosphorus modifying agent (c) and finally the organotin component (b).

5. The process of claim 4 wherein (c) is triphenylphosphine or a trialkylphosphine wherein the alkyl groups contain from 2 to 6 carbon atoms and the molar ratio of (b) to (a) is between 0.9:1 and 1.1:1.

6. The process of claim 5 conducted at a temperature of 90° to 180° C using about 0.0006 mole to 0.05 mole tungsten hexachloride per mole of the olefin.

7. The process of claim 6 wherein (b) is tetrabutyl tin and (c) is triphenylphosphine or tri-n-butylphosphine.

8. The process of claim 7 wherein the olefin is 1-decene or 1-octene.

* * * * *